(12) United States Patent
Baker et al.

(10) Patent No.: US 9,895,068 B2
(45) Date of Patent: Feb. 20, 2018

(54) PULSE OXIMETER WITH WAIT-TIME INDICATION

(75) Inventors: Clark R. Baker, Newman, CA (US); Daryl Bordon, Livermore, CA (US)

(73) Assignee: Covidien LP, Mansfield, MA (US)

(*) Notice: Subject to any disclaimer, the term of this patent is extended or adjusted under 35 U.S.C. 154(b) by 1964 days.

(21) Appl. No.: 12/165,241

(22) Filed: Jun. 30, 2008

(65) Prior Publication Data

US 2009/0326335 A1    Dec. 31, 2009

(51) Int. Cl.
*A61B 5/00* (2006.01)
*A61B 5/024* (2006.01)
*A61B 5/1455* (2006.01)

(52) U.S. Cl.
CPC ...... *A61B 5/02416* (2013.01); *A61B 5/14551* (2013.01); *A61B 5/742* (2013.01); *A61B 5/7445* (2013.01); *A61B 2560/0276* (2013.01)

(58) Field of Classification Search
CPC . A61B 5/02416; A61B 5/14551; A61B 5/742; A61B 5/7445; A61B 2560/0276
USPC ........ 600/300, 301, 309, 310, 322, 323, 324
See application file for complete search history.

(56) References Cited

U.S. PATENT DOCUMENTS

| | | | |
|---|---|---|---|
| 3,638,640 A | 2/1972 | Shaw | |
| 4,714,341 A | 12/1987 | Hamaguri et al. | |
| 4,805,623 A | 2/1989 | Jöbsis | |
| 4,807,631 A | 2/1989 | Hersh et al. | |
| 4,911,167 A | 3/1990 | Corenman et al. | |
| 4,913,150 A | 4/1990 | Cheung et al. | |

(Continued)

FOREIGN PATENT DOCUMENTS

| | | |
|---|---|---|
| DE | 19640807 | 9/1997 |
| DE | 19647877 | 5/1998 |

(Continued)

OTHER PUBLICATIONS

Bushman, J.P., et al.; "Principles and Problems of Calibration of Fetal Oximeters," Biomedizinishe Technik, vol. 42, pp. 265-266 (1997).

(Continued)

*Primary Examiner* — Max Hindenburg
*Assistant Examiner* — Jonathan M Foreman

(57) ABSTRACT

The present disclosure provides a system and method for determination and indication of the time remaining before a patient's physical characteristics are displayed on a monitor. The indication may be a numeric count-down, a progress bar, a clock face, an audible signal, or any other time and/or progress indication. The approximate wait-time may be determined, for example, by adding the known, generally fixed durations of characteristic determination processes to the calculated, variable durations of characteristic determination processes. Exemplary processes which may have generally fixed durations include monitor boot-up, sensor validation, and sensor calibration. Exemplary processes which may have variable durations include sensor location determination and pulsation detection. The sum of the pre-determined and calculated durations may be an approximate wait-time, which is indicated to a caregiver via visual or audible display. If a process takes longer than anticipated or an unexpected event occurs, the wait-time indication may be modified to reflect the longer anticipated wait-time.

20 Claims, 4 Drawing Sheets

(56) References Cited

U.S. PATENT DOCUMENTS

| | | |
|---|---|---|
| 4,936,679 A | 6/1990 | Mersch |
| 4,938,218 A | 7/1990 | Goodman et al. |
| 4,971,062 A | 11/1990 | Hasebe et al. |
| 4,972,331 A | 11/1990 | Chance |
| 4,974,591 A | 12/1990 | Awazu et al. |
| 5,028,787 A | 7/1991 | Rosenthal et al. |
| 5,065,749 A | 11/1991 | Hasebe et al. |
| 5,084,327 A | 1/1992 | Stengel |
| 5,119,815 A | 6/1992 | Chance |
| 5,122,974 A | 6/1992 | Chance |
| 5,167,230 A | 12/1992 | Chance |
| 5,190,038 A | 3/1993 | Polson et al. |
| 5,246,003 A | 9/1993 | DeLonzor |
| 5,247,931 A | 9/1993 | Norwood |
| 5,263,244 A | 11/1993 | Centa et al. |
| 5,275,159 A | 1/1994 | Griebel |
| 5,279,295 A | 1/1994 | Martens et al. |
| 5,297,548 A | 3/1994 | Pologe |
| 5,355,880 A | 10/1994 | Thomas et al. |
| 5,372,136 A | 12/1994 | Steuer et al. |
| 5,385,143 A | 1/1995 | Aoyagi |
| 5,390,670 A | 2/1995 | Centa et al. |
| 5,410,474 A * | 4/1995 | Fox ................ 600/300 |
| 5,413,099 A | 5/1995 | Schmidt et al. |
| 5,469,845 A | 11/1995 | DeLonzor et al. |
| 5,482,036 A | 1/1996 | Diab et al. |
| 5,483,646 A | 1/1996 | Uchikoga |
| 5,553,614 A | 9/1996 | Chance |
| 5,564,417 A | 10/1996 | Chance |
| 5,575,285 A | 11/1996 | Takanashi et al. |
| 5,611,337 A | 3/1997 | Bukta |
| 5,630,413 A | 5/1997 | Thomas et al. |
| 5,645,059 A | 7/1997 | Fein et al. |
| 5,645,060 A | 7/1997 | Yorkey |
| 5,680,857 A | 10/1997 | Pelikan et al. |
| 5,692,503 A | 12/1997 | Keunstner |
| 5,730,124 A | 3/1998 | Yamauchi |
| 5,758,644 A | 6/1998 | Diab et al. |
| 5,779,631 A | 7/1998 | Chance |
| 5,782,757 A | 7/1998 | Diab et al. |
| 5,786,592 A | 7/1998 | Hök |
| 5,830,136 A | 11/1998 | DeLonzor et al. |
| 5,830,139 A | 11/1998 | Abreu |
| 5,831,598 A | 11/1998 | Kauffert et al. |
| 5,842,981 A | 12/1998 | Larsen et al. |
| 5,871,442 A | 2/1999 | Madarasz et al. |
| 5,873,821 A | 2/1999 | Chance et al. |
| 5,920,263 A | 7/1999 | Huttenhoff et al. |
| 5,995,855 A | 11/1999 | Kiani et al. |
| 5,995,856 A | 11/1999 | Mannheimer et al. |
| 5,995,859 A | 11/1999 | Takahashi |
| 6,011,986 A | 1/2000 | Diab et al. |
| 6,064,898 A | 5/2000 | Aldrich |
| 6,081,742 A | 6/2000 | Amano et al. |
| 6,088,607 A | 7/2000 | Diab et al. |
| 6,120,460 A | 9/2000 | Abreu |
| 6,134,460 A | 10/2000 | Chance |
| 6,150,951 A | 11/2000 | Olejniczak |
| 6,154,667 A | 11/2000 | Miura et al. |
| 6,163,715 A | 12/2000 | Larsen et al. |
| 6,181,958 B1 | 1/2001 | Steuer et al. |
| 6,181,959 B1 | 1/2001 | Schöllermann et al. |
| 6,230,035 B1 | 5/2001 | Aoyagi et al. |
| 6,266,546 B1 | 7/2001 | Steuer et al. |
| 6,285,895 B1 | 9/2001 | Ristolainen et al. |
| 6,312,393 B1 | 11/2001 | Abreu |
| 6,353,750 B1 | 3/2002 | Kimura et al. |
| 6,397,091 B2 | 5/2002 | Diab et al. |
| 6,415,166 B1 | 7/2002 | Van Hoy et al. |
| 6,415,236 B2 | 7/2002 | Kobayashi et al. |
| 6,419,671 B1 | 7/2002 | Lemberg |
| 6,438,399 B1 | 8/2002 | Kurth |
| 6,461,305 B1 | 10/2002 | Schnall |
| 6,466,809 B1 | 10/2002 | Riley |
| 6,487,439 B1 | 11/2002 | Skladnev et al. |
| 6,493,069 B1 * | 12/2002 | Nagashimada et al. ........ 356/39 |
| 6,501,974 B2 | 12/2002 | Huiku |
| 6,501,975 B2 | 12/2002 | Diab et al. |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,580,086 B1 | 6/2003 | Schulz et al. |
| 6,591,122 B2 | 7/2003 | Schmitt |
| 6,594,513 B1 | 7/2003 | Jobsis et al. |
| 6,606,509 B2 | 8/2003 | Schmitt |
| 6,606,511 B1 | 8/2003 | Ali et al. |
| 6,615,064 B1 | 9/2003 | Aldrich |
| 6,618,042 B1 | 9/2003 | Powell |
| 6,622,095 B2 | 9/2003 | Kobayashi et al. |
| 6,654,621 B2 | 11/2003 | Palatnik et al. |
| 6,654,624 B2 | 11/2003 | Diab et al. |
| 6,658,276 B2 | 12/2003 | Kianl et al. |
| 6,658,277 B2 | 12/2003 | Wasserman |
| 6,662,030 B2 | 12/2003 | Khalil et al. |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,675,031 B1 | 1/2004 | Porges et al. |
| 6,678,543 B2 | 1/2004 | Diab et al. |
| 6,684,090 B2 | 1/2004 | Ali et al. |
| 6,690,958 B1 | 2/2004 | Walker et al. |
| 6,697,658 B2 | 2/2004 | Al-Ali |
| 6,708,048 B1 | 3/2004 | Chance |
| 6,711,424 B1 | 3/2004 | Fine et al. |
| 6,711,425 B1 | 3/2004 | Reuss |
| 6,714,245 B1 | 3/2004 | Ono |
| 6,731,274 B2 | 5/2004 | Powell |
| 6,785,568 B2 | 8/2004 | Chance |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,829,496 B2 | 12/2004 | Nagai et al. |
| 6,850,053 B2 | 2/2005 | Daalmans et al. |
| 6,863,652 B2 | 3/2005 | Huang et al. |
| 6,873,865 B2 | 3/2005 | Steuer et al. |
| 6,889,153 B2 | 5/2005 | Dietiker |
| 6,898,451 B2 | 5/2005 | Wuori |
| 6,939,307 B1 | 9/2005 | Dunlop |
| 6,947,780 B2 | 9/2005 | Scharf |
| 6,949,081 B1 | 9/2005 | Chance |
| 6,961,598 B2 | 11/2005 | Diab |
| 6,983,178 B2 | 1/2006 | Fine et al. |
| 6,985,762 B2 | 1/2006 | Brashears et al. |
| 6,993,371 B2 | 1/2006 | Kiani et al. |
| 6,996,427 B2 | 2/2006 | Ali et al. |
| 7,024,235 B2 | 4/2006 | Melker et al. |
| 7,027,849 B2 | 4/2006 | Al-Ali |
| 7,030,749 B2 | 4/2006 | Al-Ali |
| 7,035,697 B1 | 4/2006 | Brown |
| 7,047,056 B2 | 5/2006 | Hannula et al. |
| 7,127,278 B2 | 10/2006 | Melker et al. |
| 7,162,306 B2 | 1/2007 | Caby et al. |
| 7,209,775 B2 | 4/2007 | Bae et al. |
| 7,236,811 B2 | 6/2007 | Schmitt |
| 7,263,395 B2 | 8/2007 | Chan et al. |
| 7,272,426 B2 | 9/2007 | Schmid |
| 7,373,193 B2 | 5/2008 | Al-Ali et al. |
| 2001/0005773 A1 | 6/2001 | Larsen et al. |
| 2001/0020122 A1 | 9/2001 | Steuer et al. |
| 2001/0039376 A1 | 11/2001 | Steuer et al. |
| 2001/0044700 A1 | 11/2001 | Kobayashi et al. |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0085952 A1 | 7/2002 | Ellingboe et al. |
| 2002/0111748 A1 | 8/2002 | Kobayashi et al. |
| 2002/0133068 A1 | 9/2002 | Huiku |
| 2002/0156354 A1 | 10/2002 | Larson |
| 2002/0161287 A1 | 10/2002 | Schmitt |

(56) References Cited

U.S. PATENT DOCUMENTS

| | | |
|---|---|---|
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |
| 2003/0055324 A1 | 3/2003 | Wasserman |
| 2003/0060693 A1 | 3/2003 | Monfre et al. |
| 2003/0139687 A1 | 7/2003 | Abreu |
| 2003/0144584 A1 | 7/2003 | Mendelson |
| 2003/0220548 A1 | 11/2003 | Schmitt |
| 2003/0220576 A1 | 11/2003 | Diab |
| 2004/0010188 A1 | 1/2004 | Wasserman |
| 2004/0054270 A1 | 3/2004 | Pewzner et al. |
| 2004/0087846 A1 | 5/2004 | Wasserman |
| 2004/0107065 A1 | 6/2004 | Al-Ali |
| 2004/0127779 A1 | 7/2004 | Steuer et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0230106 A1 | 11/2004 | Schmitt et al. |
| 2005/0080323 A1 | 4/2005 | Kato |
| 2005/0101850 A1 | 5/2005 | Parker |
| 2005/0113651 A1 | 5/2005 | Wood et al. |
| 2005/0113656 A1 | 5/2005 | Chance |
| 2005/0168722 A1 | 8/2005 | Forstner et al. |
| 2005/0177034 A1 | 8/2005 | Beaumont |
| 2005/0192488 A1 | 9/2005 | Bryenton et al. |
| 2005/0203357 A1 | 9/2005 | Debreczeny et al. |
| 2005/0228248 A1 | 10/2005 | Dietiker |
| 2005/0267346 A1 | 12/2005 | Faber et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0015022 A1* | 1/2006 | Cho et al. ............. 600/316 |
| 2006/0020181 A1 | 1/2006 | Schmitt |
| 2006/0030763 A1 | 2/2006 | Mannheimer et al. |
| 2006/0052680 A1 | 3/2006 | Diab |
| 2006/0058683 A1 | 3/2006 | Chance |
| 2006/0064024 A1 | 3/2006 | Schnall |
| 2006/0074321 A1 | 4/2006 | Kouchi et al. |
| 2006/0195028 A1 | 8/2006 | Hannula et al. |
| 2006/0224058 A1 | 10/2006 | Mannheimer |
| 2006/0247501 A1 | 11/2006 | Ali |
| 2006/0258921 A1 | 11/2006 | Addison et al. |
| 2007/0135717 A1* | 6/2007 | Uenishi et al. ............. 600/485 |
| 2008/0027368 A1 | 1/2008 | Kollar et al. |
| 2008/0103375 A1 | 5/2008 | Kiani |
| 2011/0137134 A1* | 6/2011 | Hemmerling et al. ......... 600/301 |

FOREIGN PATENT DOCUMENTS

| | | |
|---|---|---|
| DE | 20318882 | 3/2004 |
| EP | 0352923 | 7/1989 |
| EP | 0497021 | 1/1991 |
| EP | 0531631 | 6/1992 |
| EP | 0615723 | 3/1993 |
| EP | 1491135 | 4/1993 |
| EP | 0702931 | 9/1995 |
| EP | 0194105 | 2/1998 |
| JP | 63275325 | 11/1988 |
| JP | 2013450 | 1/1990 |
| JP | 2111343 | 4/1990 |
| JP | 2237544 | 9/1990 |
| JP | 3124073 | 5/1991 |
| JP | 3134144 | 6/1991 |
| JP | 3170866 | 7/1991 |
| JP | 3238813 | 10/1991 |
| JP | 4174648 | 6/1992 |
| JP | 4191642 | 7/1992 |
| JP | 4332536 | 11/1992 |
| JP | 5049624 | 3/1993 |
| JP | 6098881 | 4/1994 |
| JP | 7124138 | 5/1995 |
| JP | 7136150 | 5/1995 |
| JP | 8256996 | 10/1996 |
| JP | 9192120 | 7/1997 |
| JP | 10216115 | 8/1998 |
| JP | 10337282 | 12/1998 |
| JP | 11019074 | 1/1999 |
| JP | 2003194714 | 7/2003 |
| JP | 2003210438 | 7/2003 |
| JP | 2003275192 | 9/2003 |
| JP | 2003339678 | 12/2003 |
| JP | 2004008572 | 1/2004 |
| JP | 2004113353 | 4/2004 |
| JP | 2004135854 | 5/2004 |
| JP | 2004159810 | 6/2004 |
| JP | 2004166775 | 6/2004 |
| JP | 2004194908 | 7/2004 |
| JP | 2004202190 | 7/2004 |
| JP | 2004248819 | 9/2004 |
| JP | 2004290412 | 10/2004 |
| JP | 2004290545 | 10/2004 |
| JP | 2005034472 | 2/2005 |
| WO | WO09101678 | 7/1990 |
| WO | WO09200513 | 1/1992 |
| WO | WO9221281 | 12/1992 |
| WO | WO9309711 | 5/1993 |
| WO | WO9313706 | 7/1993 |
| WO | WO9316629 | 9/1993 |
| WO | WO9403102 | 2/1994 |
| WO | WO9512349 | 5/1995 |
| WO | WO9639927 | 12/1996 |
| WO | WO9749330 | 12/1997 |
| WO | WO9817174 | 4/1998 |
| WO | WO9842249 | 10/1998 |
| WO | WO9842251 | 10/1998 |
| WO | WO9843071 | 10/1998 |
| WO | WO9932030 | 7/1999 |
| WO | WO0021438 | 4/2000 |
| WO | WO0116577 | 3/2001 |
| WO | WO0117421 | 3/2001 |
| WO | WO0140776 | 6/2001 |
| WO | WO0176461 | 10/2001 |
| WO | WO0176471 | 10/2001 |
| WO | WO03009750 | 2/2003 |
| WO | WO03011127 | 2/2003 |
| WO | WO03039326 | 5/2003 |
| WO | WO2005009221 | 2/2005 |
| WO | WO2005010568 | 2/2005 |
| WO | WO2005065540 | 7/2005 |

OTHER PUBLICATIONS

Pickett, John, et al.; "Pulse Oximetry and PPG Measurements in Plastic Surgery," Proceedings—19th International Conference—IEEE/EMBS, Chicago, Illinois, Oct. 30-Nov. 2, 1997, pp. 2330-2332.

Leahy, Martin J., et al.; "Sensor Validation in Biomedical Applications," IFAC Modeling and Control in Biomedical Systems, Warwick, UK; pp. 221-226 (1997).

Barreto, Armando B., et al.; "Adaptive LMS Delay Measurement in dual Blood Volume Pule Signals for Non-Invasive Monitoring," IEEE, pp. 117-120 (1997).

DeKock, Marc, "Pulse Oximetry Probe Adhesive Disks: a Potential for Infant Aspiration." Anesthesiology, vol. 89, pp. 1603-1604 (1998).

East, Christine E., et al.; "Fetal Oxygen Saturation and Uterine Contractions During Labor," American Journal of Perinatology, vol. 15, pp. 345-349 (Jun. 1998).

Such, Hans Olaf; "Optoelectronic Non-Invasive Vascular Diagnostics Using multiple Wavelength and Imaging Approach," Dissertation, (1998).

Todd, Brian, et al.; "The Identification of Peaks in Physiological Signals," Computers and Biomedical Research, vol. 32, pp. 322-335 (1999).

Vicenzi, Martin N.; "Transesophageal versus Surface Pulse Oximetry in Intensive Care Unit Patients," Crit. Care Med,; vol. 28, No. 7, pp. 2268-2270 (2000).

Goldman, Julian M.; "Masimo Signal Extraction Pulse Oximetry," Journal of Clinical Monitoring and Computing, vol. 16, pp. 475-483 (2000).

(56) References Cited

OTHER PUBLICATIONS

Coetzee, Frans M.; "Noise-Resistant Pulse Oximetry Using a Synthetic Reference Signal," IEEE Transactions on Biomedical Engineering, vol. 47, No. 8, Aug. 2000, pp. 1018-1026.

Nilsson, Lena, et al.; "Monitoring of Respiratory Rate in Postoperative Care Using a New Photoplethysmographic Technique," Journal of Clinical Monitoring and Computing, vol. 16, pp. 309-315 (2000).

Kaestle, S.; "Determining Artifact Sensitivity of New Pulse Oximeters in Laboratory Using Signals Obtained from Patient," Biomedizinishce Technik, vol. 45 (2000).

Belal, Suliman Yousef, et al.; "A Fuzzy System for Detecting Distorted Plethysomogram Pulses in Neonates and Pediatric Patents," Physiol. Meas., vol. 22, pp. 397-412 (2001).

Earthrowl-Gould, T., et al.; "Chest and Abdominal Surface Motion Measurement for Continous Monitoring of Respiratory Function," Proc. Instn Mech Engrs, V215, Part H; pp. 515-520 (2001).

Chan, K.W., et al.; "17.3: Adaptive Reduction of Motion Artifact from Photoplethysmographic Recordings using a Variable Step-Size LMS Fileter," IEEE, pp. 1343-1346 (2002).

Koga, I., et al.; "Sigmoid colonic reflectance pulse oximetry and tonometry in a porcine experimental hypoperfusion shock model," Acta Anaesthesiol Scand, vol. 46, pp. 1212-1216 (2002).

Cyrill, D., et al.; "Adaptive Comb Filter for Quasi-Periodic Physiologic Signals," Proceedings of the 25th Annual International Conference of the IEEE EMBS, Cancun, Mexico, Sep. 17-21, 2003; pp. 2439-2442.

Stetson, Paul F.; "Determining Heart Rate from Noisey Pulse Oximeter Signals Using Fuzzy Logic," The IEEE International Conference on Fuzzy Systems, St. Louis, Missouri, May 25-28, 2003; pp. 1053-1058.

Lee, C.M., et al.; "Reduction of motion artifacts from photoplethysmographic recordings using wavelet denoising approach," IEEE EMBS Asian-Pacific Conference on Biomedical Engineering, Oct. 20-22, 2003; pp. 194-195.

Itoh, K., et al.; "Pulse Oximeter," Toyaku Zasshi (Toyaku Journal), vol. 25, No. 8, pp. 50-54 (2003) (Article in Japanese—contains English summary of article).

Nakagawa, M., et al.; "Oxygen Saturation Monitor," Neonatal Monitoring, vol. 26, No. 5, pp. 536-539 (2003) (Article in Japanese—contains English summary of article).

Johansson, A.; "Neural network for photoplethysmographic respiratory rate monitoring," Medical & Biological Engineering & Computing, vol. 41, pp. 242-248 (2003).

Mannheimer, Paul D., et al.; "The influence of Larger Subcutaneous Blood Vessels on Pulse Oximetry," Journal of clinical Monitoring and Computing, vol. 18, pp. 179-188 (2004).

Wendelken, Suzanne, et al.; "The Feasibility of Using a Forehead Reflectance Pulse Oximeter for Automated Remote Triage," IEEE, pp. 180-181 (2004).

Lopez-Silva, S.M., et al.; "Transmittance Photoplethysmography and Pulse Oximetry With Near Infrared Laser Diodes," IMTC 2004—Instrumentation and Measurement Technology Conference, Como, Italy, May 18-20, 2004; pp. 718-723.

Sugino, Shigekzau, et al.; "Forehead is as sensitive as finger pulse oximetry during general anesthesia," Can J. Anesth.; General Anesthesia, vol. 51, No. 5; pp. 432-436 (2004).

Addison, Paul S., et al.; "A novel time-frequency-based 3D Lissajous figure method and its application to the determination of oxygen saturation from the photoplethysmogram," Institute of Physic Publishing, Meas. Sci. Technol., vol. 15, pp. L15-L18 (2004).

Jovovanov, E., et al.; "Reconfigurable intelligent Sensors for Health Monitoring: A case Study of Pulse Oximeter Sensor," Proceedings o the 26th Annual International conference of the IEEE EMBS, San Francisco, California, Sep. 1-5, 2004, pp. 4759-4762.

Nuhr, M., et al.: "Forehead SpO2 monitoring compared to finger SpO2 recording in emergency transport," Anaesthesia, vol. 59, pp. 390-393 (2004).

Jonnson, P.O. "Patent Cooperation Treaty PCT Written Opinion of the International Searching Authority"; Apr. 20, 2007; 12pp.; European Patent Office; Berlin.

Cysewska-Sobusaik, Anna; "Metrological Problems With noninvasive Transillumination of Living Tissues," Proceedings of SPIE, vol. 4515, pp. 15-24 (2001).

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Relente, A.R., et al.; "Characterization and Adaptive Filtering of Motion Artifacts in Pulse Oximetry using Accelerometers," Proceedings of the Second joint EMBS/BMES Conference, Houston, Texas, Oct. 23-26, 2002; pp. 1769-1770.

Lutter, N., et al.; "Accuracy of Noninvasive Continuous Blood Pressure; Measurement Utilising the Pulse Transit Time," Journal of clinical Monitoring and Computing, vol. 17, Nos. 7-8, pp. 469 (2002).

Odagiri, Y.; "Pulse Wave Measuring Device," Micromechatronics, vol. 42, No. 3, pp. 6-11. Sep. 1998. (Article in Japanese—contains English summary of article).

Edrich, Thomas, et al.; "Can the Blood Content of the Tissues be Determined Optically During Pulse Oximetry Without Knowledge of the Oxygen Saturation?—An In-Vitro Investigation," Proceedings of the 20th Annual International Conference of the IEEE Engine; Oct. 29-Nov. 1, 1998.

Hamilton, Patrick S., et al.; "Effect of Adaptive Motion-Artifact Reduction on QRS Detection," Biomedical Instrumentation & Technology, pp. 197-202. May/Jun. 2000.

Kim, J.M., et al.; "Signal Processing Using Fourier & Wavelet Transform," pp. II-310-II-311. Jul. 15-19, 2001.

Huang, J. et al.; "Low Power Motion Tolerant Pulse Oximetry," Abstracts, A7, p. S103. Mar. 8-9, 2002.

Neumann, R. et al.; "Fourier Artifact suppression Technology Provides Reliable SpO2,," Abstracts, A11, p. S105. Mar. 8-9, 2002.

\* cited by examiner

PULSE OXIMETER WITH WAIT-TIME INDICATION

BACKGROUND

The present disclosure relates generally to medical devices, and, more particularly, to a pulse oximeter having a wait-time and/or progress indication.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of healthcare, caregivers (e.g., doctors and other healthcare professionals) often desire to monitor certain physiological characteristics of their patients. Accordingly, a wide variety of monitoring devices have been developed for monitoring many such physiological characteristics. These monitoring devices often provide doctors and other healthcare personnel with information that facilitates provision of the best possible healthcare for their patients. As a result, such monitoring devices have become a perennial feature of modern medicine.

One technique for monitoring physiological characteristics of a patient is commonly referred to as pulse oximetry, and the devices built based upon pulse oximetry techniques are commonly referred to as pulse oximeters. Pulse oximeters may be used to measure and monitor various blood flow characteristics of a patient. For example, a pulse oximeter may be utilized to monitor the blood oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time-varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. A photo-plethysmographic waveform, which corresponds to the cyclic attenuation of optical energy through the patient's tissue, may be generated from the detected light. Additionally, one or more of the above physiological characteristics may be calculated based generally upon the amount of light absorbed or scattered. More specifically, the light passed through the tissue may be selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Generally, the pulse oximeter begins displaying the patient's physiological characteristics after the sensor has been placed and enough time has passed for the monitor to calculate the characteristics from the data received from the sensor. In some instances, the caregiver applying the pulse oximeter sensor may expect the patient's physiological characteristics to be displayed instantly or within a very short period of time after applying the sensor. If the characteristics are not yet calculated, they will not yet be displayed, and the caregiver may erroneously believe that the sensor is misapplied. In these instances, the caregiver may reposition the sensor before the pulse oximeter has the time to calculate and display the patient's physiological characteristics. Once the sensor is repositioned, the calculations must begin again, thereby slowing down the acquisition of the patient's information. An impatient caregiver may inadvertently delay the acquisition and display of the patient's physiological characteristics by moving the sensor.

BRIEF DESCRIPTION OF THE DRAWINGS

Advantages of the disclosure may become apparent upon reading the following detailed description and upon reference to the drawings in which.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When a caregiver applies a medical monitor, such as a pulse oximeter, to a patient, the caregiver must generally wait for some time to pass before the monitor displays the physical characteristic being monitored. For example, when a caregiver applies a pulse oximetry sensor to a patient and turns on the monitor, some time passes before the monitor is able to display the patient's $SpO_2$. The time delay may be due to monitor start-up processes, sensor calibration, signal detection, and so forth. In some cases, an impatient caregiver might not wait long enough for the monitor to begin displaying the physical characteristic before deciding that the sensor is misapplied and moving it. This action forces the monitor to restart the physical characteristic determination, thereby further delaying the posting of the physical parameter on the monitor. Accordingly, it may be desirable to provide the caregiver with a wait-time and/or progress indication so that the caregiver leaves the sensor in place long enough for the physical characteristic to be determined. The indication may also alert the caregiver when the sensor should be reapplied or the system should be checked.

Figure 1:
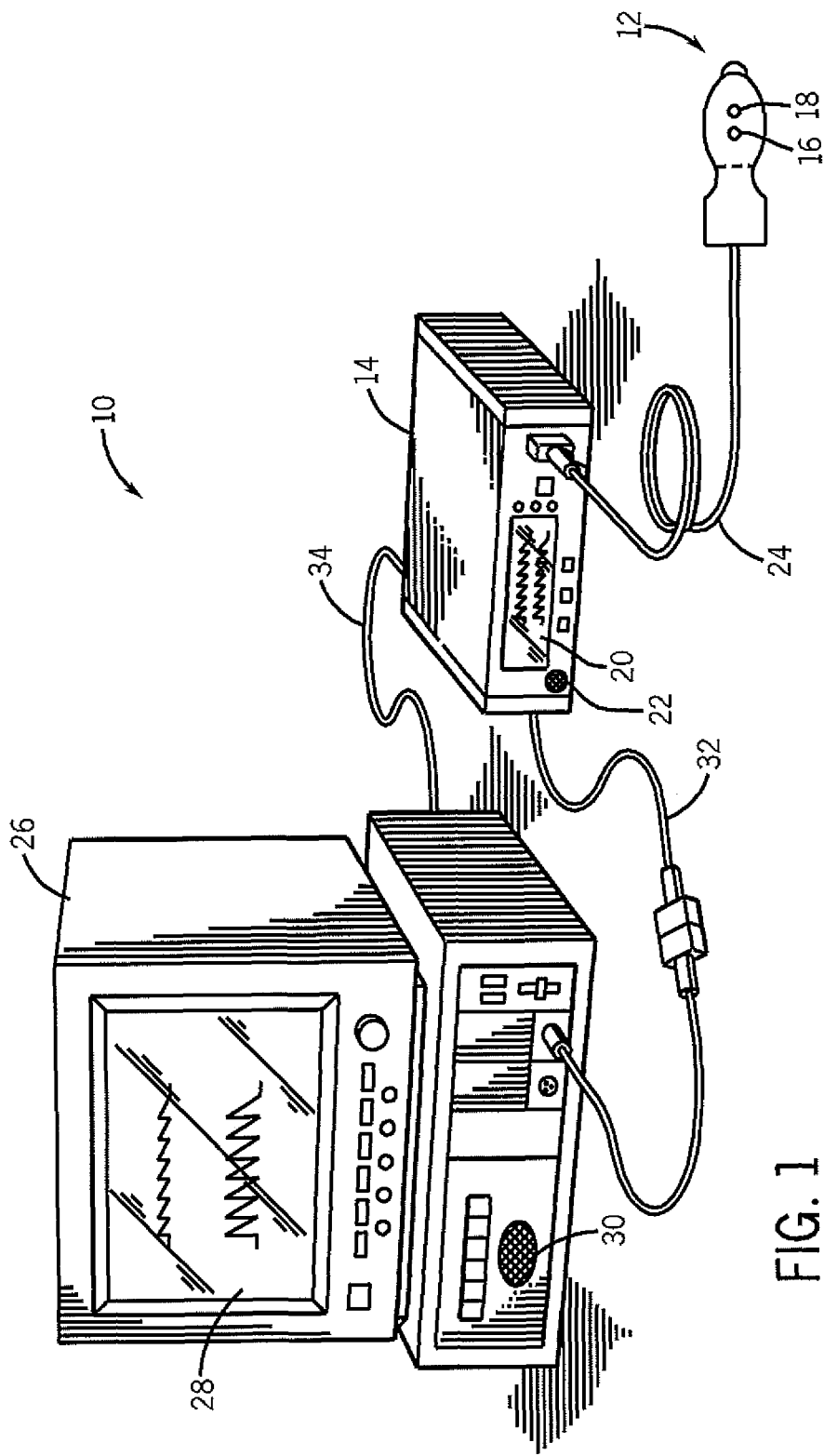
FIG. 1 is a perspective view of a pulse oximeter coupled to a multi-parameter patient monitor and a sensor in accordance with embodiments.

FIG. 1 is a perspective view of such a pulse oximetry system 10 in accordance with an embodiment. The system 10 includes a sensor 12 and a pulse oximetry monitor 14. The sensor 12 includes an emitter 16 for emitting light at certain wavelengths into a patient's tissue and a detector 18 for detecting the light after it is reflected and/or absorbed by the patient's tissue. The monitor 14 may be capable of calculating physiological characteristics received from the sensor 12 relating to light emission and detection. Further, the monitor 14 includes a display 20 capable of displaying the physiological characteristics, other information about the system, and/or alarm indications. The monitor 14 also includes a speaker 22 to provide an audible alarm in the event that the patient's physiological characteristics exceed a threshold. The sensor 12 is communicatively coupled to the monitor 14 via a cable 24. However, in other embodiments a wireless transmission device or the like may be utilized instead of or in addition to the cable 24.

In the illustrated embodiment the pulse oximetry system 10 also includes a multi-parameter patient monitor 26. In addition to the monitor 14, or alternatively, the multi-parameter patient monitor 26 may be capable of calculating physiological characteristics and providing a central display 28 for information from the monitor 14 and from other medical monitoring devices or systems. For example, the multi-parameter patient monitor 26 may display a patient's $SpO_2$ and pulse rate information from the monitor 14 and blood pressure from a blood pressure monitor on the display 28. Additionally, the multi-parameter patient monitor 26 may indicate an alarm condition via the display 28 and/or a speaker 30 if the patient's physiological characteristics are found to be outside of the normal range. The monitor 14 may be communicatively coupled to the multi-parameter patient monitor 26 via a cable 32 or 34 coupled to a sensor input port or a digital communications port, respectively. In addition, the monitor 14 and/or the multi-parameter patient monitor 26 may be connected to a network to enable the sharing of information with servers or other workstations.

Figure 2:
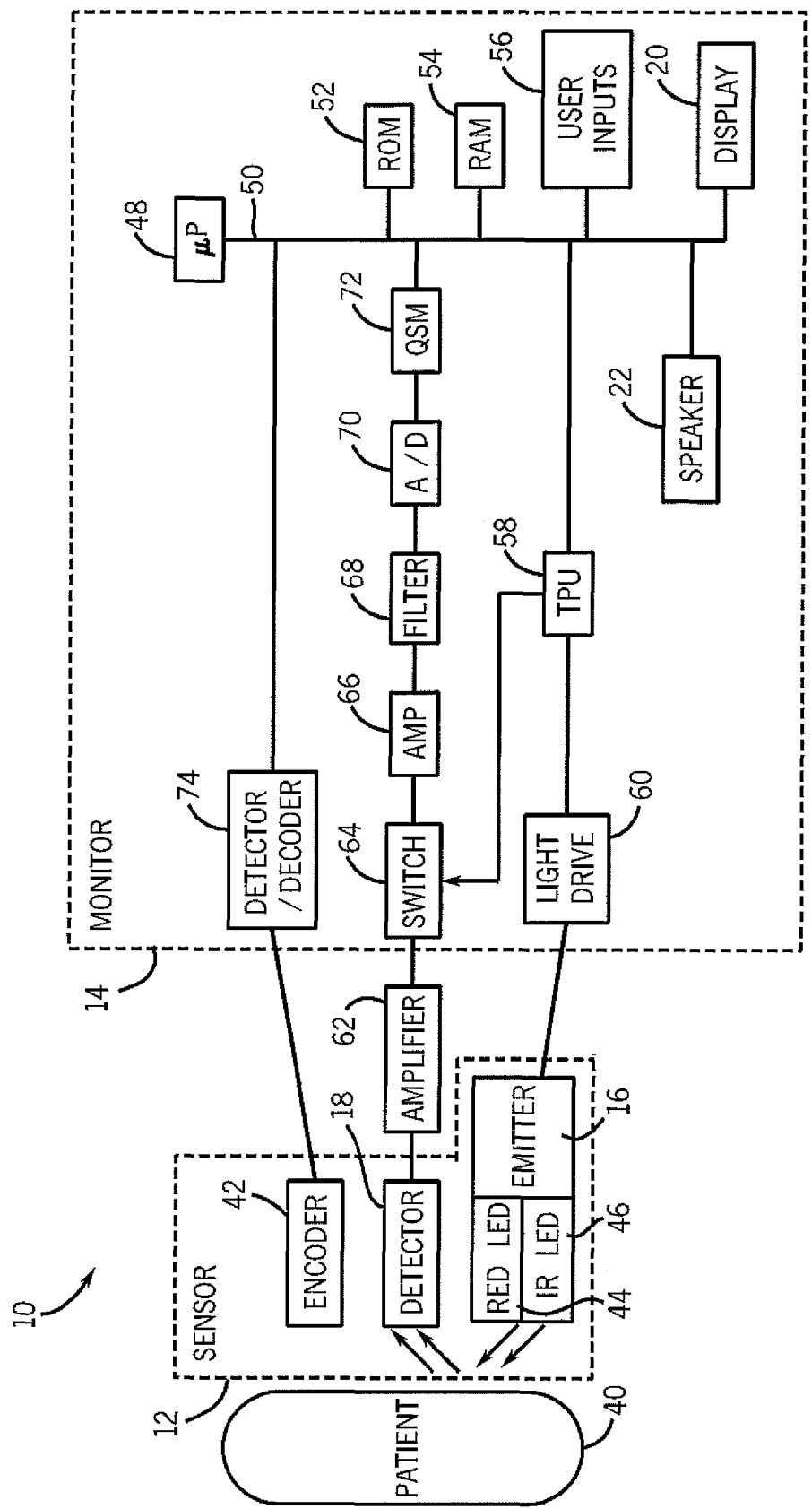
FIG. 2 is a block diagram of the pulse oximeter and sensor coupled to a patient in accordance with embodiments.

FIG. 2 is a block diagram of the exemplary pulse oximetry system 10 of FIG. 1 coupled to a patient 40 in accordance with present embodiments. One such pulse oximeter that may be used in the implementation of the present disclosure is the OxiMax® N-600x™ available from Nellcor Puritan Bennett LLC, but the following discussion may be applied to other pulse oximeters and medical devices. Specifically, certain components of the sensor 12 and the monitor 14 are illustrated in FIG. 2. The sensor 12 may include the emitter 16, the detector 18, and an encoder 42. It should be noted that the emitter 16 may be capable of emitting at least two wavelengths of light, e.g., RED and IR, into a patient's tissue 40. Hence, the emitter 16 may include a RED LED 44 and an IR LED 46 for emitting light into the patient's tissue 40 at the wavelengths used to calculate the patient's physiological characteristics. In certain embodiments, the RED wavelength may be between about 600 nm and about 700 nm, and the IR wavelength may be between about 800 nm and about 1000 nm. Alternative light sources may be used in other embodiments. For example, a single wide-spectrum light source may be used, and the detector 18 may be capable of detecting certain wavelengths of light. In another example, the detector 18 may detect a wide spectrum of wavelengths of light, and the monitor 14 may process only those wavelengths which are of interest. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

In one embodiment, the detector 18 may be capable of detecting the intensity of light at the RED and IR wavelengths. In operation, light enters the detector 18 after passing through the patient's tissue 40. The detector 18 may convert the intensity of the received light into an electrical signal. The light intensity may be directly related to the absorbance and/or reflectance of light in the tissue 40. That is, when more light at a certain wavelength is absorbed or reflected, less light of that wavelength is typically received from the tissue by the detector 18. After converting the received light to an electrical signal, the detector 18 may send the signal to the monitor 14, where physiological characteristics may be calculated based at least in part on the absorption of the RED and IR wavelengths in the patient's tissue 40.

The encoder 42 may contain information about the sensor 12, such as what type of sensor it is (e.g., whether the sensor is intended for placement on a forehead or digit) and the wavelengths of light emitted by the emitter 16. This information may allow the monitor 14 to select appropriate algorithms and/or calibration coefficients for calculating the patient's physiological characteristics. The encoder 42 may, for instance, be a coded resistor which stores values corresponding to the type of the sensor 12 and/or the wavelengths of light emitted by the emitter 16. These coded values may be communicated to the monitor 14, which determines how to calculate the patient's physiological characteristics. In another embodiment, the encoder 42 may be a memory on which one or more of the following information may be stored for communication to the monitor 14: the type of the sensor 12; the wavelengths of light emitted by the emitter 16; and the proper calibration coefficients and/or algorithms to be used for calculating the patient's physiological characteristics. Exemplary pulse oximetry sensors capable of cooperating with pulse oximetry monitors are the OxiMax® sensors available from Nellcor Puritan Bennett LLC.

Signals from the detector 18 and the encoder 42 may be transmitted to the monitor 14. The monitor 14 generally may include processors 48 connected to an internal bus 50. Also connected to the bus may be a read-only memory (ROM) 52, a random access memory (RAM) 54, user inputs 56, the display 20, or the speaker 22. A time processing unit (TPU) 58 may provide timing control signals to a light drive circuitry 60 which controls when the emitter 16 is illuminated and the multiplexed timing for the RED LED 44 and the IR LED 46. The TPU 58 control the gating-in of signals from detector 18 through an amplifier 62 and a switching circuit 64. These signals may be sampled at the proper time, depending upon which light source is illuminated. The received signal from the detector 18 may be passed through an amplifier 66, a low pass filter 68, and an analog-to-digital converter 70. The digital data may then be stored in a queued serial module (QSM) 72 for later downloading to the RAM 54 as the QSM 72 fills up. In one embodiment, there may be multiple separate parallel paths having the amplifier 66, the filter 68, and the A/D converter 70 for multiple light wavelengths or spectra received.

The processor(s) 48 may determine the patient's physiological characteristics, such as $SpO_2$ and pulse rate, using various algorithms and/or look-up tables based generally on the value of the received signals corresponding to the light received by the detector 18. Signals corresponding to information about the sensor 12 may be transmitted from the encoder 42 to a decoder 74. The decoder 74 may translate these signals to enable the microprocessor to determine the proper method for calculating the patient's physiological characteristics, for example, based generally on algorithms or look-up tables stored in the ROM 52. In addition, or alternatively, the encoder 42 may contain the algorithms or look-up tables for calculating the patient's physiological characteristics. In certain embodiments, the display 20 may exhibit an indication of the approximate time remaining for determination and display of the patient's physiological characteristics.

Figure 3:
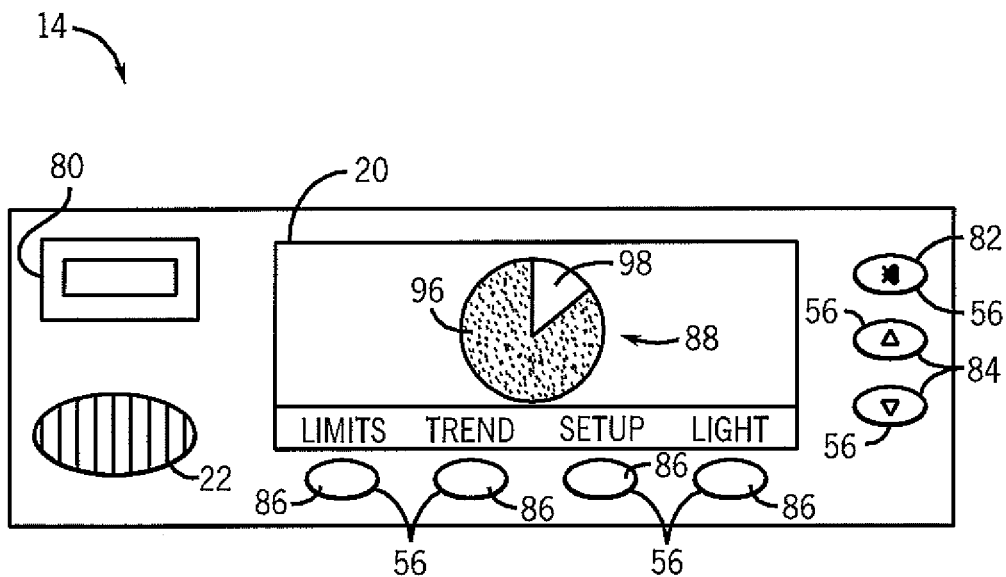
FIGS. 3-4 are exemplary graphical user interfaces of the pulse oximeter in accordance with embodiments.
Figure 4:
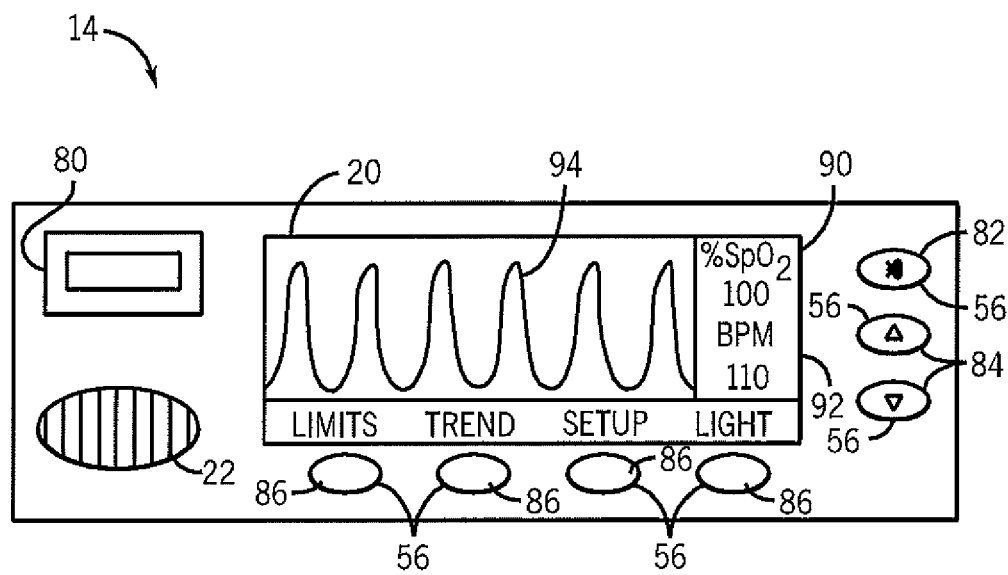

FIGS. 3-4 illustrate an exemplary monitor 14 for use in the system 10 (FIG. 1). The monitor 14 may generally include the display 20, the speaker 22, the user inputs 56, and a communication port 80 for coupling the sensor 12 to the monitor 14. The user inputs 56 may enable the caregiver to control the monitor 14 and change settings. For example, an alarm silence button 82 may enable the caregiver to silence an audible alarm (e.g., when the patient is being cared for), and volume buttons 84 may enable the caregiver to adjust the volume of the alarm and/or any other indicators emitted from the speaker 22. In addition, soft keys 86 may correspond to variable functions, as displayed on the display 20. The soft keys 86 may provide access to further data and/or setting displays. Soft keys 86 provided on the display 20 may enable the caregiver to see and/or change alarm thresholds, view different trend data, change characteristics of the display 20, turn a backlight on or off, or perform other functions.

In accordance with an embodiment when the monitor 14 is turned on and the sensor 12 is applied to the patient 40, the display 20 may initially show a wait-time/progress indication 88 before the patient's physical characteristics are displayed (FIG. 3). The wait-time/progress indication 88 may be, for example, an estimated numeric wait time or a graphic illustrating progress in the determination of the patient's physical characteristics. Upon determination of the physical characteristics, the display 20 may show the characteristics, such as, for example, an $SpO_2$ value 90 (i.e., percentage), a pulse rate 92 (i.e., beats per minute), and a plethysmographic waveform (i.e., a plot 94) (FIG. 4). In some instances, the $SpO_2$ value 90 may take longer to determine than the pulse rate 92 and/or the plethysmographic waveform 94, and therefore may be displayed after the other characteristics are displayed. Accordingly, the wait-time/progress indication 88 may be displayed to show only the time remaining before the patient's $SpO_2$ value 90 is determined.

In the illustrated embodiment, the wait-time/progress indication 88 is displayed in place of the physical characteristics, however in other embodiments the indication 88 may be displayed in another location (e.g., a dedicated area on the display 20). In addition, the exemplary wait-time/progress indication 88 illustrated in FIG. 3 is a graphic illustrating the approximate time remaining as a clock face, where a shaded area 96 indicates the approximate time remaining before the patient's physical characteristics are to be displayed. The shaded area 96 may decrease, and a clear area 98 may increase, as progress is made in determining the physical characteristics. It should be understood that in practice the meanings of the shaded area 96 and the clear area 98 may be reversed, or colors may be used. In other embodiments, the wait-time/progress indication 88 may be a numeric count-down, a progress bar, or another indication of the approximate time remaining before display of the patient's characteristics. When progress is not being made in determining the patient's physical characteristics, the wait-time/progress indication 88 may indicate such. For example, the shaded area 96 may expand, filling in the area 98 that had been cleared. In the case of a numeric count-down, the wait-time/progress indication 88 may stop counting down or may begin to count tip to account for the additional anticipated wait-time. In another embodiment, an error signal may replace the wait-time indication 88 to indicate to the caregiver that the monitor 14 is not making progress in determining the patient's physical characteristics. The caregiver may then, for example, reposition the sensor 12 or check the connections in the system 10 (FIG. 1). Additionally, or instead, an audible signal from the speaker 22, such as a count-down or a variable beeping sound, may indicate the approximate time remaining before display of the patient's characteristics.

Figure 5:
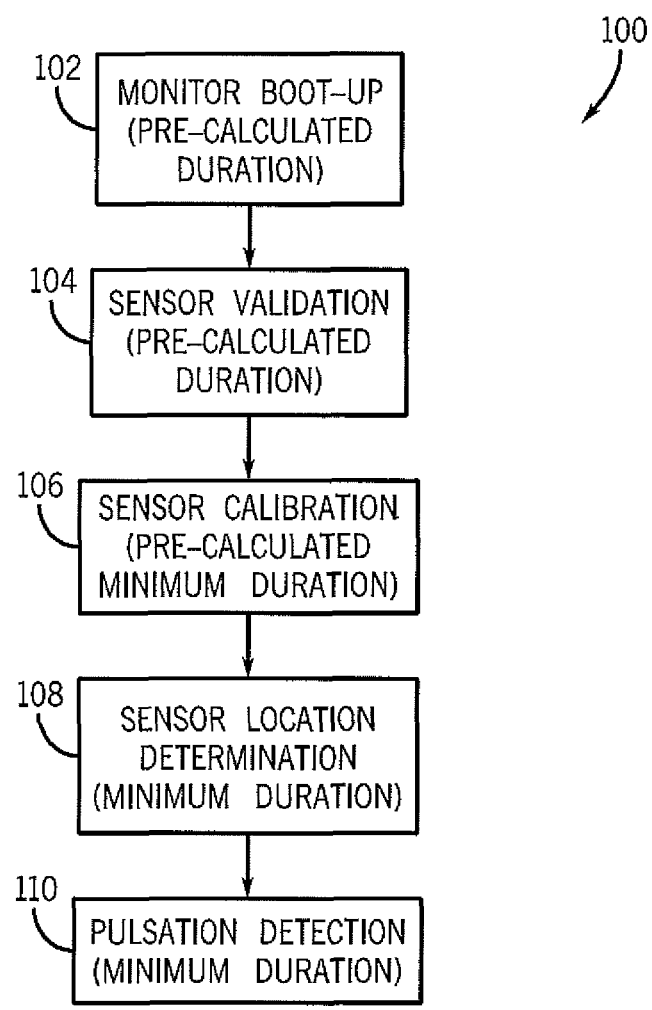
FIG. 5 is a flow chart of an exemplary wait-time calculation in accordance with embodiments.

In order to calculate the approximate wait-time, the monitor 14 may include software which analyzes the progress of the physical characteristic determination, as illustrated in a flow chart 100 in FIG. 5. Wait-time calculation may be performed by the microprocessor 48 (FIG. 2), another processor in the monitor 14, or on an auxiliary monitor. Exemplary processes which may affect the time it takes to determine the patient's physical characteristics may include, for example, monitor boot-up 102, sensor validation 104, sensor calibration 106, sensor location detection 108, and pulsation detection 110. Some of these processes may have generally fixed durations (i.e., the process may take approximately the same amount of time every time it is performed), while other processes may have very situation-specific durations (i.e., the process completion time may vary greatly depending on various circumstances). For example, the monitor boot-up process 102, although different for every type of monitor 14, may be generally fixed for a given monitor model. In contrast, the sensor location detection 108 may be performed quickly or slowly depending on the quality of the signals received by the monitor 14, the location of the sensor 12 on the patient 40, or other variables.

Generally, the initial wait-time may be based at least in part on the durations of the generally fixed processes and minimum duration estimates of the variable processes. For example, the fixed processes may include the monitor boot-up 102, the sensor validation 104, and the sensor calibration 106. An exemplary monitor boot-up process 102 may include checking the RAM 54 (FIG. 2) for errors, measuring offset voltages, setting up the display 20 (FIG. 1), and so forth. The sensor validation process 104 may be performed to determine if a valid sensor 12 is connected to the monitor 14. For example, some sensors may not be compatible with certain monitors. The calibration coefficients for the sensor may also be read and/or decrypted. The sensor calibration process may include, for example, turning of the LEDs 44 and 46 (FIG. 2), measuring the baseline voltage from the amplifiers 62 and 66 with the LEDs off, and adjusting the amplifier gains and LED settings to optimize the signal strengths. Although the completion time for the sensor calibration 106 may vary slightly, a minimum duration for the process 106 may be pre-calculated and/or pre-determined and included in the initial estimated wait time. For the fixed processes, all of these steps may take approximately the same amount of time whenever they are performed. Accordingly, the fixed processes may have a pre-calculated duration which is automatically included in the wait time estimation whenever the monitor 14 is turned on and/or the sensor 12 is applied to the patient 40.

In addition to the fixed process durations, minimum durations for the variable processes may be included in the initial wait time estimation. If a step in the process takes longer than initially anticipated, the wait-time/progress indicator 88 may be increased to compensate for the delay or paused to indicate that the process is not progressing as anticipated. Exemplary variable processes may include the sensor location detection 108 and the pulsation detection 110. Because the sensor location detection 108 depends greatly on the quality of the sensor signal, the time it takes for the monitor 14 to determine the location of the sensor 12 may vary greatly. For example, if the sensor 12 is designed for application to a finger but is erroneously applied to a forehead, the monitor 14 may take longer to determine that the sensor 12 is misapplied than it would take if the sensor 12 had been correctly applied to the finger. In instances such as this, the wait-time/progress indication 88 may pause (i.e., stop showing progress) or increase (e.g., count up or begin refilling the clear area 98 (FIG. 3). If the monitor 14 determines that the physiological parameter cannot be determined due to a bad signal (e.g., improper sensor placement), the caregiver may be alerted via the wait-time/progress indication 88 or another signal (e.g., an alarm, a graphic, a significantly increased wait-time indication 88, cessation of progress in the progress indication 88, and so forth).

Because the patient's physical characteristics may be based generally on detected pulsations, the pulsations may need to be detected before the characteristics may be displayed. Accordingly, the estimated duration of the pulsation detection process 110 may also be included in the wait-time calculation. As with the sensor location detection 108, the duration of pulsation detection 110 may vary greatly depending on the signal quality from the sensor 12, correct placement of the sensor 12, and other factors. A minimum time estimate may be included in the initial wait-time calculation, and if the pulsation detection process 110 takes longer than the minimum estimated duration, the wait-time calculation may be modified (e.g., the wait-time/progress indication 88 may indicate an increased wait-time or lack of progress). In addition, if unexpected events occur which impede the determination of the patient's physical characteristics, the wait-time/progress indication 88 may again indicate an increased wait-time or lack of progress, or an error signal (e.g., a graphic, a text warning, an audible alarm, and so forth) may be provided.

While only certain features have been illustrated and described herein, many modifications and changes will occur to those skilled in the art. It is, therefore, to be understood that the appended claims are intended to cover all such modifications and changes as fall within their true spirit.

What is claimed is:

1. A physiological monitor comprising:
a display; and
a processor configured to cause display of a progress indication indicative of a time remaining before a physiological parameter is initially displayed on the display prior to initial posting of the physiological parameter, wherein the processor is configured to determine an approximate wait-time until the physiological parameter is initially displayed and to determine the progress indication based at least in part upon the approximate wait-time, and wherein the processor is configured to analyze the progress towards the initial posting of the physiological parameter and to modify the approximate wait-time and the progress indication based at least in part upon the analysis.

2. The monitor of claim 1, wherein the progress indication comprises a numeric indication.

3. The monitor of claim 2, wherein the numeric indication comprises an approximate wait-time countdown.

4. The monitor of claim 1, wherein the progress indication comprises a graphical indication.

5. The monitor of claim 4, wherein the graphical indication comprises a progress bar or a clock face.

6. The monitor of claim 1, comprising a speaker configured to provide an audible progress indication prior to initial posting of the physiological parameter.

7. The monitor of claim 1, wherein the processor is configured to calculate the physiological parameter.

8. The monitor of claim 1, comprising a pulse oximeter or a multi-parameter monitor.

9. The monitor of claim 1, wherein the physiological parameter comprises a blood oxygen saturation, a pulse rate, or a combination thereof.

10. The physiological monitor of claim 1, wherein the processor is configured to determine the approximate wait-time by combining estimated completion times for sensor validation, signal measurements, and calculation of the physiological parameter.

11. The physiological monitor of claim 1, wherein the processor is configured to determine the approximate wait-time by combining estimated completion times for one or more fixed-time processes and one or more variable-time processes.

12. A system, comprising:
a monitor, comprising:
a display; and
a processor configured to cause display of a progress indication indicative of a time remaining before a physiological parameter is initially displayed on the display prior to initial posting of the physiological parameter, wherein the processor is configured to determine an approximate wait-time until the physiological parameter is initially displayed and to determine the progress indication based at least in part upon the approximate wait-time, and wherein the processor is configured to analyze the progress towards the initial posting of the physiological parameter and to modify the approximate wait-time and the progress indication based at least in part upon the analysis; and
a sensor configured to provide information to the monitor.

13. The system of claim 12, wherein the sensor comprises a pulse oximetry sensor.

14. The system of claim 12, wherein the progress indication comprises a numeric indication.

15. The monitor of claim 12, wherein the progress indication comprises a graphical indication.

16. The system of claim 12, wherein the processor is configured to determine the approximate wait-time by combining estimated completion times for one or more fixed-time processes and one or more variable-time processes.

17. The system of claim 12, wherein the processor is configured to determine the approximate wait-time by combining estimated completion times for a predetermined sequence of internal events of the physiological monitor.

18. The system of claim 17, wherein the predetermined sequence of internal events of the physiological monitor comprises sensor validation, signal measurements, and calculation of the physiological parameter.

19. The system of claim 17, wherein the processor is configured to modify the approximate wait-time based at least in part upon an occurrence or severity of events other than the predetermined sequence of internal events of the monitor.

20. The system of claim 19, wherein the events other than the predetermined sequence of internal events of a monitor comprise sensor location detection or pulsation detection.

* * * * *